US012029464B2

(12) United States Patent
Sieh et al.

(10) Patent No.: US 12,029,464 B2
(45) Date of Patent: Jul. 9, 2024

(54) PENCIL-GRIP WIRE DRIVER OPERATED WITH DISTALLY LOCATED ACTUATOR

(71) Applicant: Conmed Corporation, Utica, NY (US)

(72) Inventors: John K. Sieh, Safety Harbor, FL (US); James McGarvey, Saint Petersburg, FL (US)

(73) Assignee: Conmed Corporation, Utica, NY (US)

(*) Notice: Subject to any disclaimer, the term of this patent is extended or adjusted under 35 U.S.C. 154(b) by 933 days.

(21) Appl. No.: 17/046,002

(22) PCT Filed: Apr. 8, 2019

(86) PCT No.: PCT/US2019/026312
§ 371 (c)(1),
(2) Date: Oct. 8, 2020

(87) PCT Pub. No.: WO2019/199666
PCT Pub. Date: Oct. 17, 2019

(65) Prior Publication Data
US 2021/0030456 A1    Feb. 4, 2021

Related U.S. Application Data

(60) Provisional application No. 62/654,618, filed on Apr. 9, 2018.

(51) Int. Cl.
A61B 17/88 (2006.01)
A61B 17/00 (2006.01)
(52) U.S. Cl.
CPC ............ A61B 17/8861 (2013.01); A61B 2017/00367 (2013.01); A61B 2017/0042 (2013.01)
(58) Field of Classification Search
CPC .................................. A61B 17/8861
See application file for complete search history.

(56) References Cited

U.S. PATENT DOCUMENTS 3,847,154 A     11/1974 Nordin
4,050,528 A *   9/1977 Foltz ............... A61B 17/1697
                                                173/217
(Continued)

FOREIGN PATENT DOCUMENTS

DE    202011052316    3/2012
EP    2702950         3/2014

OTHER PUBLICATIONS

CA Office Action dated May 17, 2023, App. No. 3094246, pp. 1-5.
(Continued)

Primary Examiner — Tessa M Matthews
(74) Attorney, Agent, or Firm — Bond, Schoeneck & King, PLLC; Frederick J. M. Price

(57) ABSTRACT

A wire driver for inserting a wire into bone. The wire driver includes a housing having proximal and distal ends, with a handpiece extending to the proximal end. The handpiece is connected to a gripping portion, which extends to the distal end. A channel extends through the gripping portion and is connected to a gripping mechanism. A drive mechanism within the handpiece is connected to the channel. The drive mechanism is configured to rotate the channel when actuated by a first actuator positioned on the handpiece (which can be on the distal end of the handpiece). A second actuator is connected to the gripping portion and the gripping mechanism. The second actuator is movable between a relaxed position and a compressed position. The user can operate both first and second actuators with the same handpiece grip. The gripping portion and second actuator are rotatable relative to the housing and first actuator.

19 Claims, 15 Drawing Sheets

(56) References Cited

U.S. PATENT DOCUMENTS

| | | | |
|---|---|---|---|
| 5,387,217 A * | 2/1995 | Sefcik | A61B 17/1697 606/86 R |
| 5,902,306 A | 5/1999 | Norman | |
| 6,050,989 A | 4/2000 | Fox et al. | |
| 6,110,174 A | 8/2000 | Nichter | |
| 6,398,551 B1 | 6/2002 | Schatz et al. | |
| 6,860,886 B1 | 3/2005 | Lee | |
| 7,156,659 B2 | 1/2007 | Pernot | |
| 7,785,328 B2 | 8/2010 | Christie et al. | |
| 8,348,959 B2 | 1/2013 | Wolford et al. | |
| 8,465,491 B2 | 6/2013 | Yedlicka et al. | |
| 8,956,342 B1 * | 2/2015 | Russo | A61B 17/1622 403/322.2 |
| 9,072,571 B2 | 7/2015 | Lancieux et al. | |
| 9,179,924 B2 | 11/2015 | Marzella | |
| 9,333,019 B2 | 5/2016 | Khosla et al. | |
| 10,105,174 B2 | 10/2018 | Krapohl | |
| 10,194,922 B2 | 2/2019 | Bono et al. | |
| 10,335,169 B2 | 7/2019 | Phillips et al. | |
| 2005/0085798 A1 | 4/2005 | Hofmann et al. | |
| 2012/0221028 A1 | 8/2012 | Shadeck et al. | |
| 2016/0262847 A1 | 9/2016 | Rickert et al. | |
| 2017/0340374 A1 * | 11/2017 | Xie | A61B 17/8897 |
| 2018/0185080 A1 * | 7/2018 | Bosshard | A61B 17/8861 |

OTHER PUBLICATIONS

International Search Report Form PCT/ISA/220, International Application No. PCT/US2019/026312, pp. 1-13, Dated Jul. 8, 2019.

JP Office Action, App. No. 2020-555047, dated Sep. 21, 2021, pp. 1-9.

KR Office Action, App. No. 10-2020-7029684, dated Apr. 28, 2022, pp. 3-11.

CA Office Action dated Nov. 23, 2021, App. No. 3094246, pp. 1-5.

* cited by examiner

PENCIL-GRIP WIRE DRIVER OPERATED WITH DISTALLY LOCATED ACTUATOR

CROSS-REFERENCES TO RELATED APPLICATIONS

This application is a National Stage Application under 35 U.S.C. 371 based on international patent application PCT/US19/26312 filed on Apr. 8, 2019, which claims priority to U.S. Provisional Patent Application Ser. No. 62/654,618, filed on Apr. 9, 2018 the entirety of which is incorporated herein by reference.

BACKGROUND OF THE INVENTION

1. Field of the Invention

The present invention is directed generally to a wire driver for inserting a wire into bone and, more particularly, to a wire driver with a distal actuator and a rotating mechanism.

2. Description of Related Art

Wire drivers are surgical devices that insert wires into bone. Pencil-grip wire drivers are devices that are shaped such that the device is typically held like a pencil, using techniques such as the cylindrical grasp, digital grasp, modified tripod grasp, or tripod grasp. Pencil-grip wire drivers have an internal mechanism that grips the wire and provides rotary force to the wire. The mechanism to grip and release the wires is controlled by an actuator. Existing wire drivers 1 have said actuator 2 located away from its distal end 3, as shown in FIG. 1, or require a second hand to move such actuator 2, as shown in FIG. 2. Thus, in order to grip or release the wire, actuation of said actuator requires the surgeons to move their fingers from the grasping position or to use a second hand to actuate the actuator, which can be a major inconvenience to the surgeon.

Therefore, there is a need for a wire driver with a distal gripping actuator and a rotating mechanism that allows a surgeon to maintain a preferred grip on the wire driver while gripping and releasing a wire extending therethrough.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to a wire driver with a distal gripping actuator and a rotating mechanism that allows a surgeon to maintain a preferred grip on the wire driver while gripping and releasing a wire extending therethrough. According to one aspect, the wire driver includes a housing having a proximal end and a distal end. The housing has a handpiece extending to the proximal end and the handpiece is connected to a gripping portion, which extends to the distal end. A channel extends through the gripping portion and is connected to a gripping mechanism. The wire driver also includes a first actuator connected to the distal end of the housing and the gripping mechanism. The first actuator is movable between a relaxed position and a compressed position.

According to another aspect, the present invention is a powered surgical tool. The surgical tool includes a housing having a proximal end and a distal end. The housing has a handpiece connected to a gripping portion. The handpiece extends to the proximal end and the gripping portion extends to the distal end. The gripping portion extends along a central longitudinal axis and the handpiece is connected to the gripping portion at an angle relative to the central longitudinal axis. The surgical tool also includes a rotating mechanism within the housing. The gripping portion is rotatable about the rotating mechanism relative to the handpiece.

According to an embodiment, the actuators identified herein can be actuated by any number of ways consistent with the basic functional concepts thereof (as summarized herein), and can include a squeezing actuation, a flipping actuation, a twisting/turning actuation, a pushing actuation and the like (as should be appreciated by those of skill in the art in conjunction with a review of this disclosure). The directions of such actuations can include alternative directions from those discussed and implemented in the examples described herein, e.g., push in the relative distal direction vs. pull in the relative proximal direction, pursuant to appropriate alternative structure to facilitate such alternative movement (as should be appreciated by those of skill in the art in conjunction with a review of this disclosure).

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures may be omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
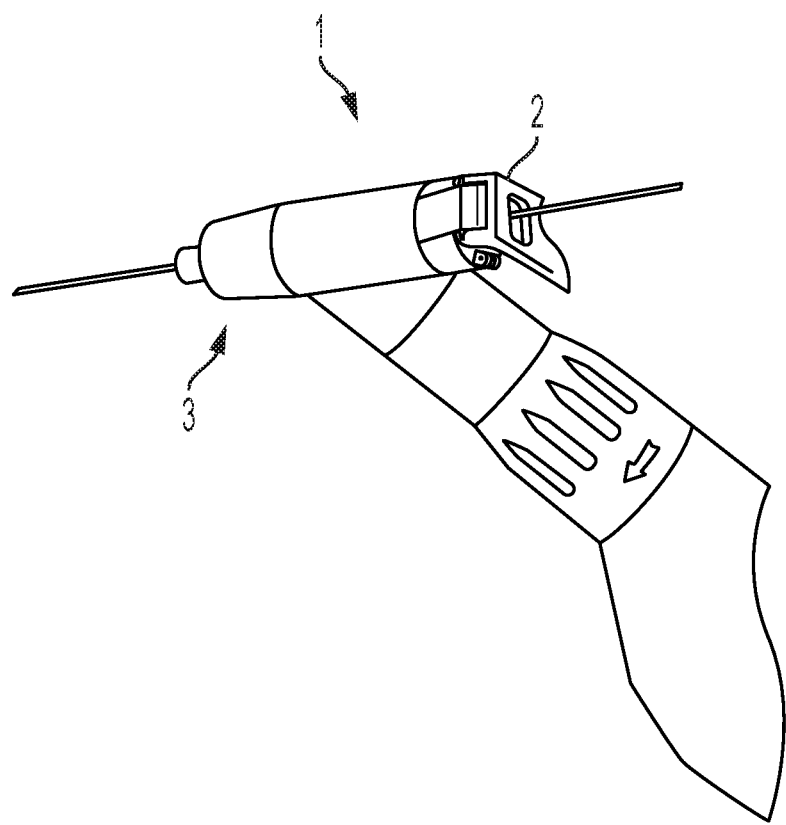
FIG. 1 is a wire driver of the prior art.
Figure 2:
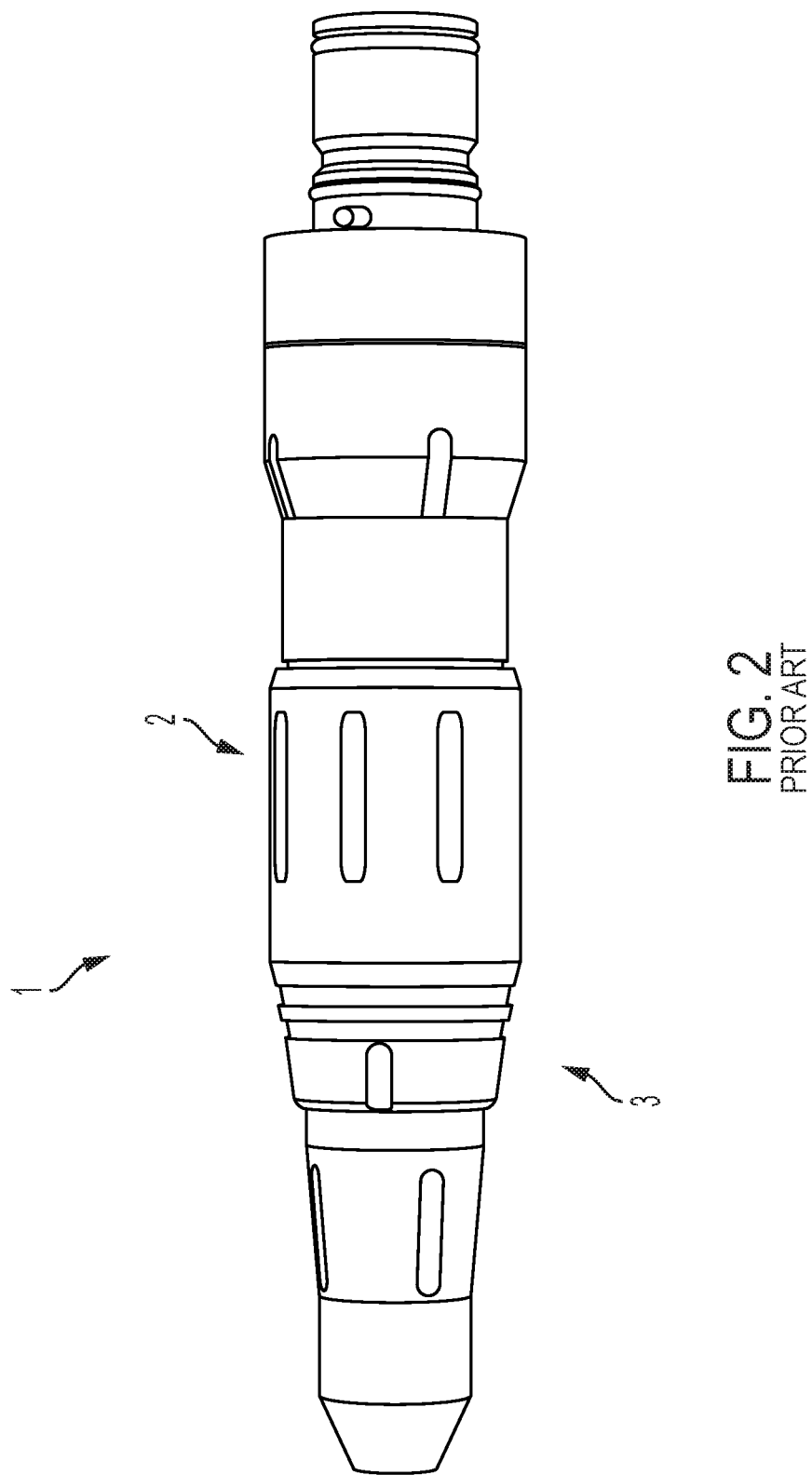
FIG. 2 is another wire driver of the prior art.
Figure 3:
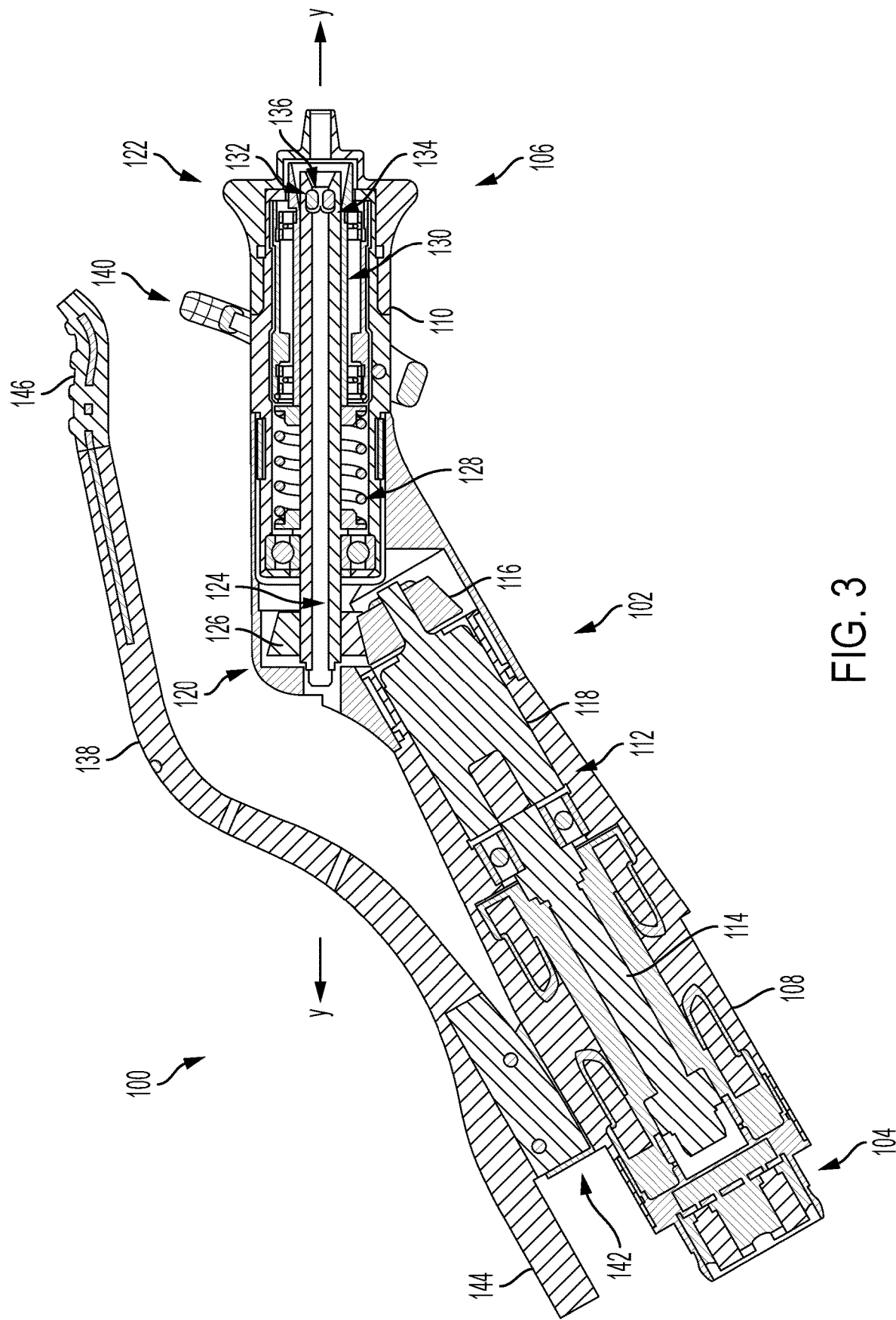
FIG. 3 is a cross-sectional side view schematic representation of a wire driver, according to an embodiment.

Referring now to the figures, wherein like reference numerals refer to like parts throughout, FIG. 3 is a cross-sectional side view schematic representation of a wire driver 100, according to an embodiment. The wire driver 100 comprises a housing 102 having a proximal end 104 and a distal end 106. In the depicted embodiment, the housing 102 comprises a handpiece 108 extending to the proximal end 104 and a gripping portion 110 extending to the distal end 106. The handpiece 108 is connected to the gripping portion 110 at an angle. Specifically, the gripping portion 110 extends along a central longitudinal y-y axis and the handpiece 108 extends proximally from the gripping portion 110 at angle relative to the central longitudinal y-y axis. According to an alternative embodiment, the handpiece 108 is not connected to the gripping portion 110 at an angle, and extends proximally from the gripping portion 110 along the y-y axis or along an axis that is at least substantially parallel to the y-y axis (see, e.g., FIG. 5-7, discussed below).

Still referring to FIG. 3, the handpiece 108 comprises a drive mechanism 112 therein such that the wire driver 100 is used as a standalone device. However, the wire driver 100 may also be an attachment to another device. In the depicted embodiment, the drive mechanism 112 is a motor and a gear assembly. In FIG. 3, the motor 114 rotates a first gear 116 of the gear assembly 118 and drives the gripping portion 110. In alternative embodiments, the drive mechanism 112 may be battery powered, pneumatic, or connected to an external power source (e.g., via a cord).

Still referring to FIG. 3, the gripping portion 110 comprises a first end 120 and a second end 122 with a channel 124 extending therethrough. The gear assembly 118 extends into the first end 120 of the gripping portion 110. In the depicted embodiment, the first end 120 of the gripping portion 110 comprises a second gear 126 of the gear assembly 118. The second gear 126 engages the first gear 116, which is powered by the motor 114. Power from the motor 114 rotates the gear assembly 118, causing rotation of the channel 124 and the wire (not shown) therein. The drive mechanism 112 performs the rotation of the channel 124 (and the wire (not shown)) when a driving actuator 138 is triggered.

As shown in FIG. 3, the driving actuator 138 is connected to the handpiece 108 of the wire driver 100. Specifically, in the depicted embodiment, the driving actuator 138 is attached at the proximal end 104 of the wire driver 100. The driving actuator 138 shown in FIG. 3 is a long curved arm connected to the handpiece 108 via a biased connector 142, such as a spring lever, for example. In the depicted embodiment, the driving actuator 138 is curved such that a distal portion 146 of the driving actuator 138 extends at least partially around and/or over the gripping portion 110 of the housing 102. A proximal portion 144 of the driving actuator 138 extends proximally relative to the biased connector 142 so that the driving actuator 138 can be easily accessed at any point along the housing 102, providing numerous grip options for the user.

Figure 4:
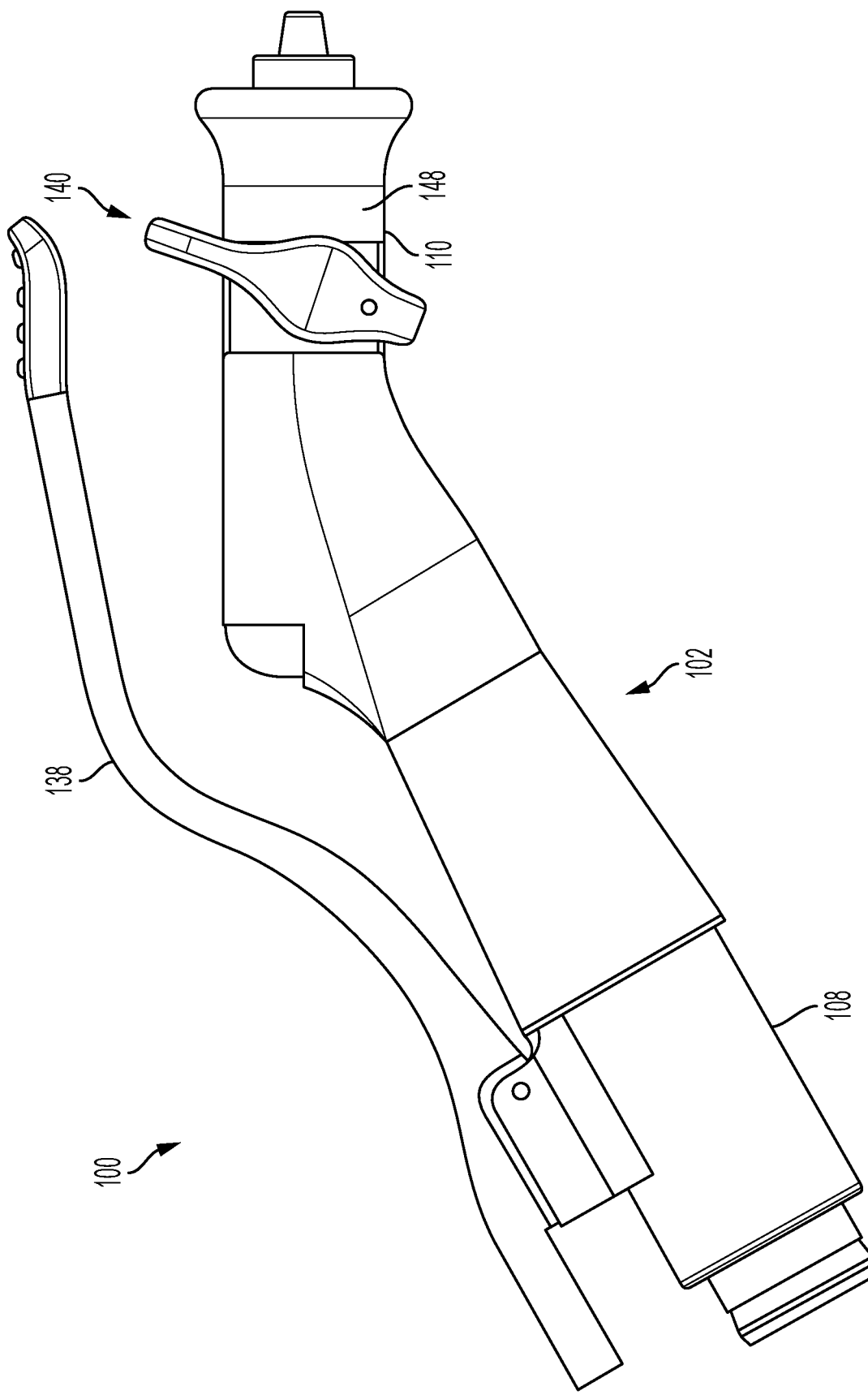
FIG. 4 is a side view schematic representation of the wire driver, according to an embodiment.

With reference still to FIG. 3, the gripping portion 110 of the wire driver 100 additionally comprises a spring assembly 128 and a distal collet 130. The channel 124 in the gripping portion 110 extends through the spring assembly 128 and the distal collet 130, as shown. The channel 124 comprises a gripping mechanism 132. In the depicted embodiment, the gripping mechanism 132 is a spindle 134 with a gripper 136 (e.g., three (or more) prong-like pieces capable of compression toward each other). The purpose of the gripping mechanism 132 is to grip and release a wire (not shown) extending through the channel 124. The gripping and release actions are performed on the wire (not shown) by a gripping actuator 140. As shown in FIG. 4, the gripping actuator 140 is a collet lever on a side 148 of the gripping portion 110.

In the embodiment shown in FIG. 3, the gripping actuator 140 is connected to the collet 130. In a relaxed position, as shown in FIGS. 3 and 4, the gripping actuator 140 is biased (by the spring assembly 128) in the distal direction. In other words, when the spring assembly 128 is in a relaxed state, the gripping actuator 140 is biased in the distal direction and causes the gripping mechanism 132 to be in the closed position and gripping the wire (not shown). To engage the gripping actuator 140, the user pulls the gripping actuator 140 in the proximal direction, which draws the collet 130 proximally against the spring assembly 128. As the collet 130 is pulled proximally by the gripping actuator 140, the gripping mechanism 132 (including the gripper 136) releases the wire (not shown) within the channel 124, placing the wire driver 100 in the compressed position (not shown).

Figure 5:
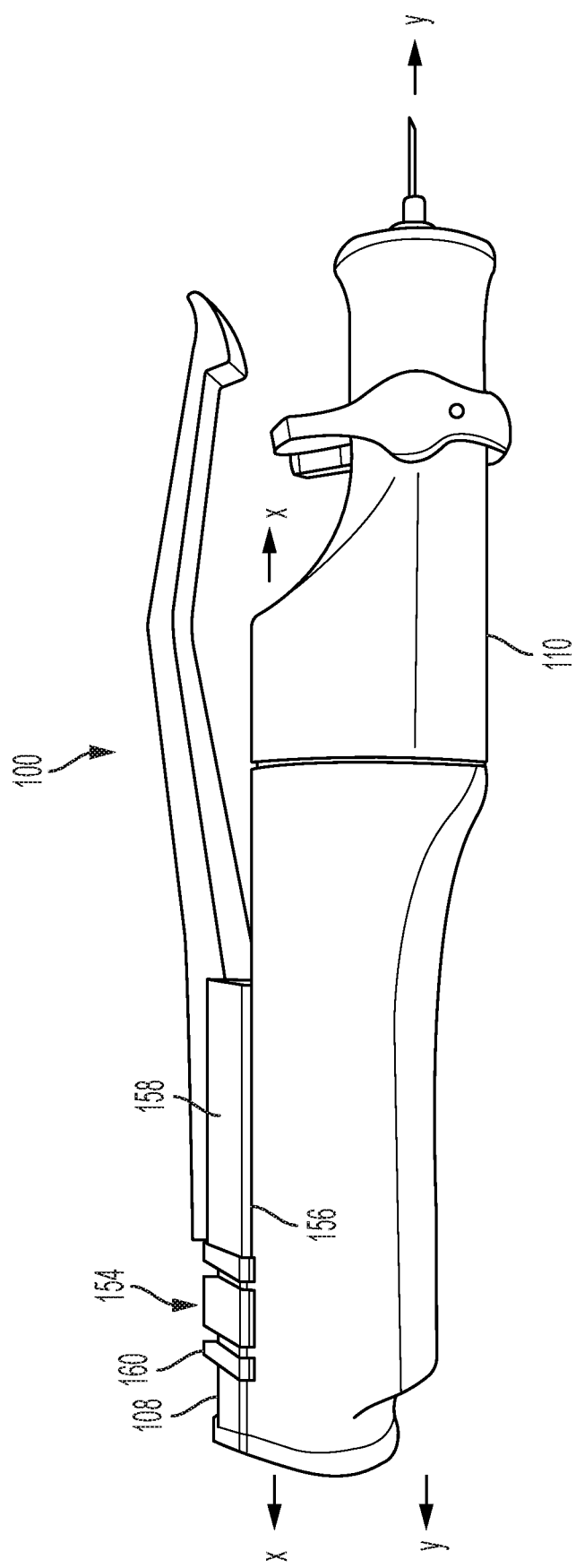
FIG. 5 is a side view schematic representation of a wire driver, according to an alternative embodiment.
Figure 6:
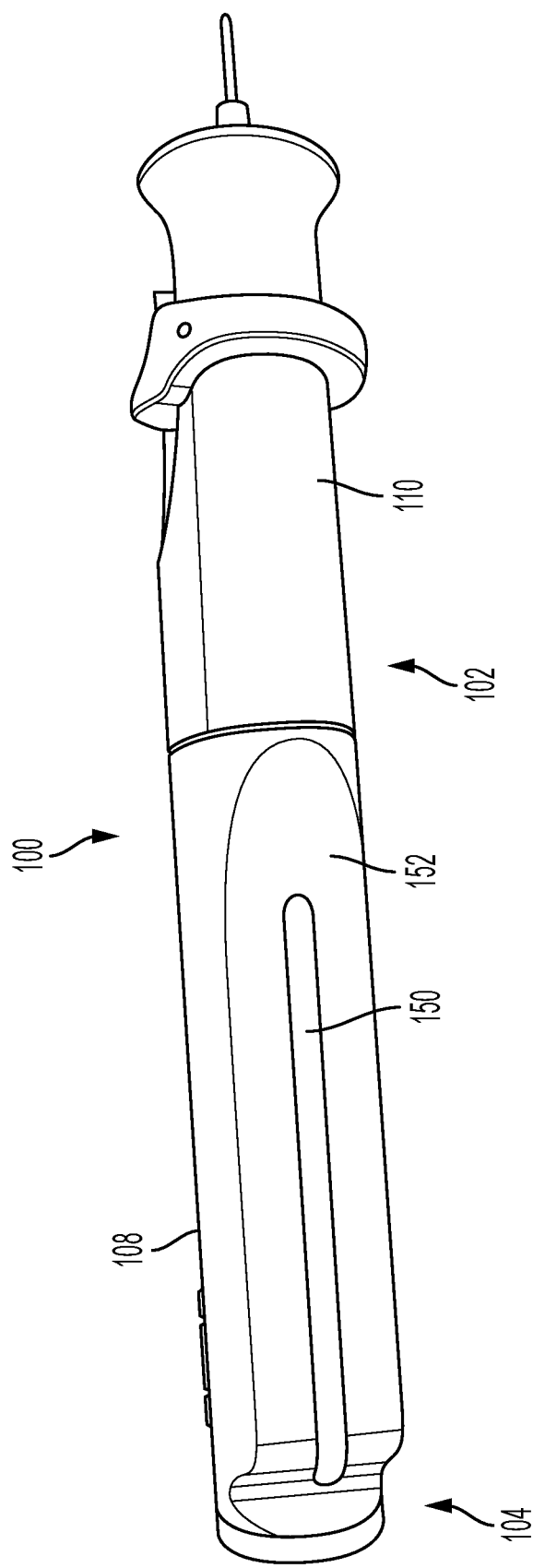
FIG. 6 is a bottom view schematic representation of the wire driver of FIG. 5.
Figure 7:
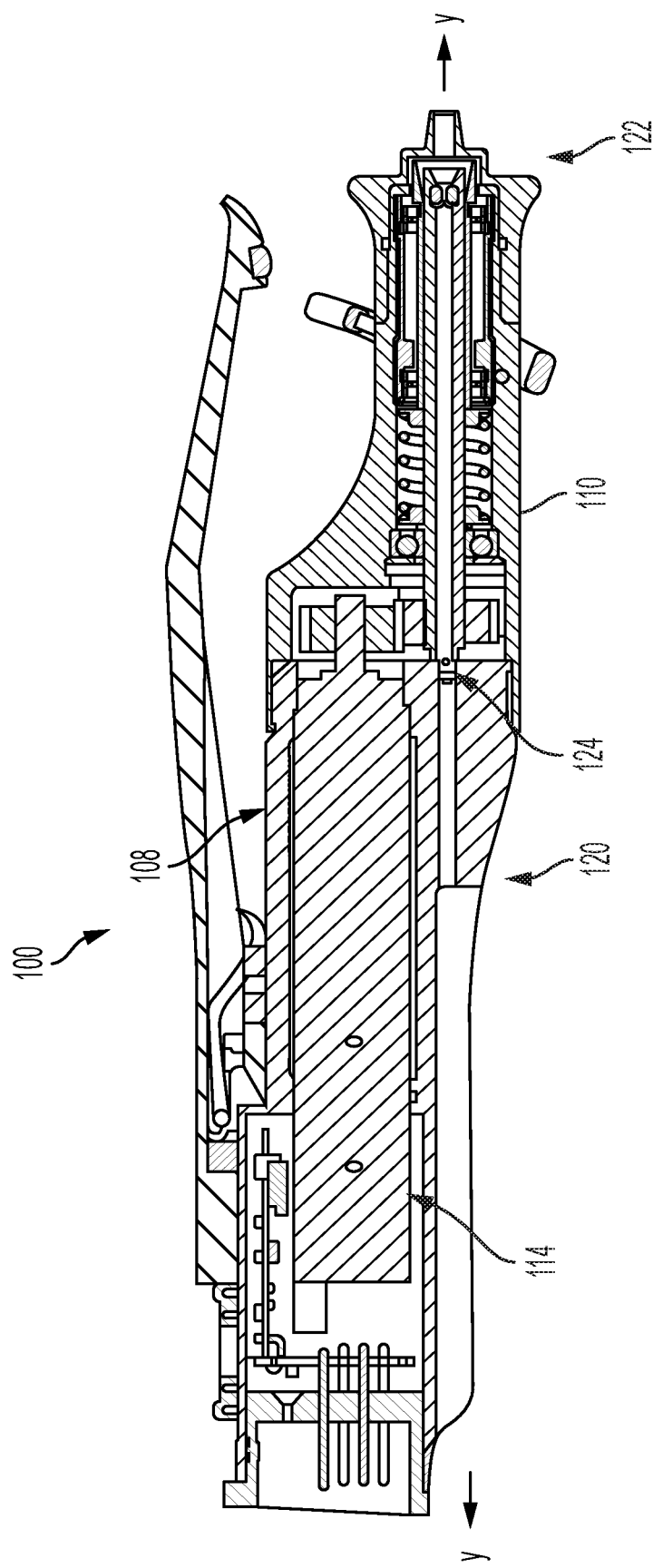
FIG. 7 cross-section side view schematic representation of the wire driver of FIG. 5.

Turning now to FIGS. 5-7, there are shown various views schematic representation of a wire driver 100, according to an alternative embodiment. In the depicted embodiment, a central longitudinal y-y axis extends through the gripping portion 110, as shown in the embodiment in FIGS. 3-4. However, in the embodiment in FIGS. 5-7, the handpiece 108 does not extend from the gripping portion 110 at an angle relative to the central longitudinal y-y axis. As shown in FIG. 5, the handpiece 108 extends along a central longitudinal x-x axis, which is approximately parallel to the central longitudinal y-y axis.

In the embodiment of the wire driver 100 depicted in FIG. 7, a channel 124 also extends through and from a first end 120 of the gripping portion 110 to a second end 122 of the gripping portion 110. In FIG. 7, the channel 124 extends along or parallel to the central longitudinal y-y axis. Further, the gripping portion 110 is slightly offset from the handpiece 108 such that the first end 120 of the gripping portion 110, has a clearance amount relative to the handpiece 108. In particular, the channel 124 extending through the gripping portion 110 bypasses the motor 114 in the handpiece 108, as shown in FIG. 7. However, the channel 124 extends and is connected to a slot 150 through at least a portion of a bottom surface 152 of the handpiece 108, as shown in FIG. 6. In the depicted embodiment, the slot 150 extends toward the proximal end 104 of the housing 102.

As also shown in FIGS. 5 and 7, the handpiece 108 comprises a sliding mechanism 154 for selectively permitting or inhibiting operation of the drive mechanism 112 when the driving actuator 138 is engaged (e.g., depressed). As shown in FIG. 5, a track (or channel) 156 extends through at a least a portion of a side surface 158 of the handpiece 108. As shown in FIG. 5, the handpiece 108 comprises a slider 160 sized and configured to slide distally and proximally along the track 156 in the handpiece 108. The user can thus move the slider 160 from a locked position to an unlocked position. In the unlocked position, the slider 160 permits operation of the drive mechanism 112. When the driving actuator 138 is engaged and in the locked position, the slider 160 inhibits operation of the drive mechanism 112 when the driving actuator 138 is engaged.

Referring now to FIGS. 8-14, there are shown various views schematic representations of a wire driver 100, according to yet another embodiment. In these embodiments, the free end portion of the gripping actuator 140 faces away from the driving actuator 138, and is pulled in the proximal direction to be actuated.

Figure 8:
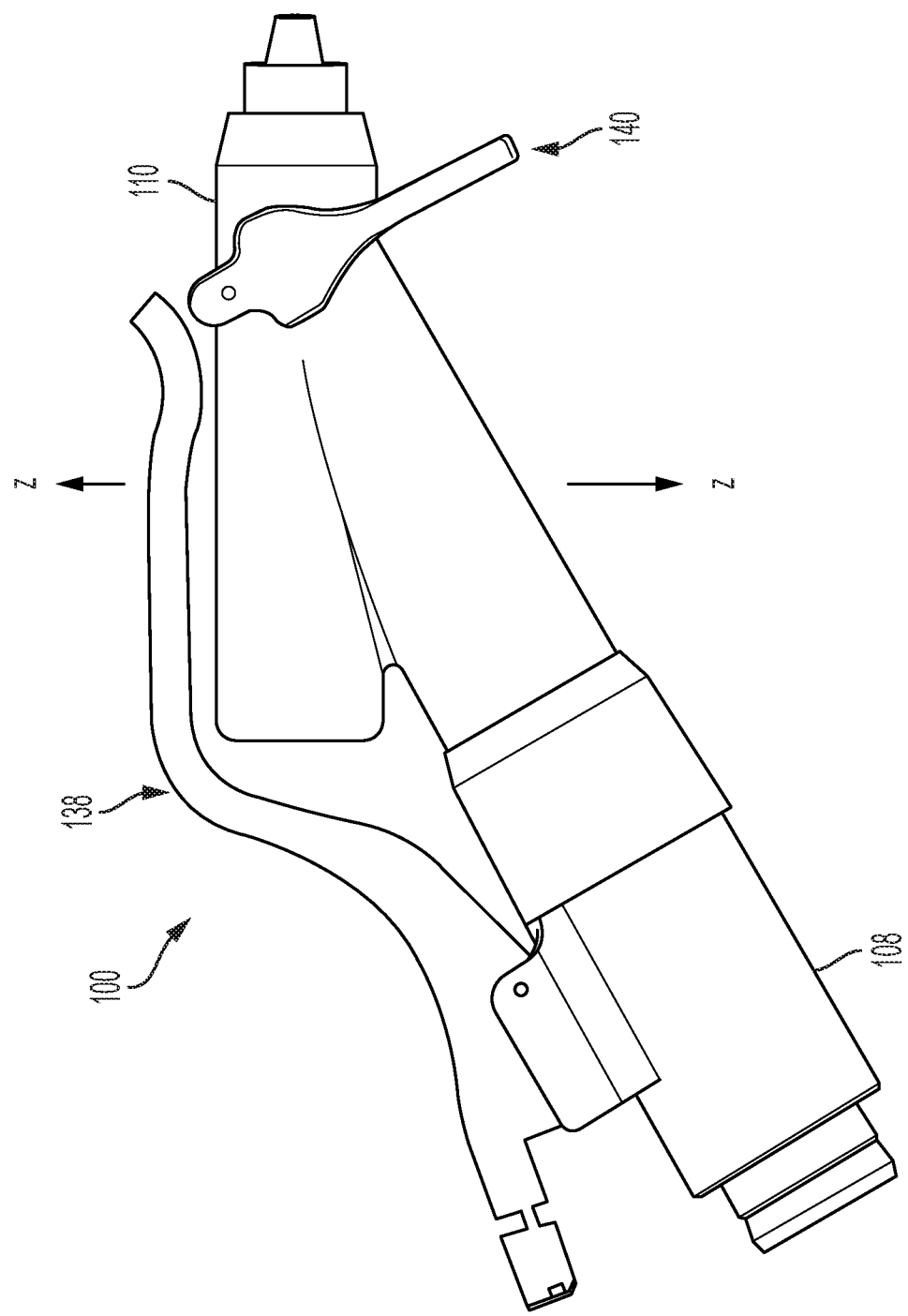
FIG. 8 is a side view schematic representation of a wire driver, according to another embodiment.

FIG. 8 shows a side view schematic representation of the wire driver 100. The wire driver 100 comprises a rotating (or indexing) mechanism 166 (FIG. 15) allowing for the wire (not shown) to be in a different plane relative to the planar axis of the handpiece 108. As shown in FIG. 8, the handpiece 108 extends along plane z-z. In the first configuration (shown in FIG. 8), the gripping portion 110 also extends along plane z-z.

Figure 15:
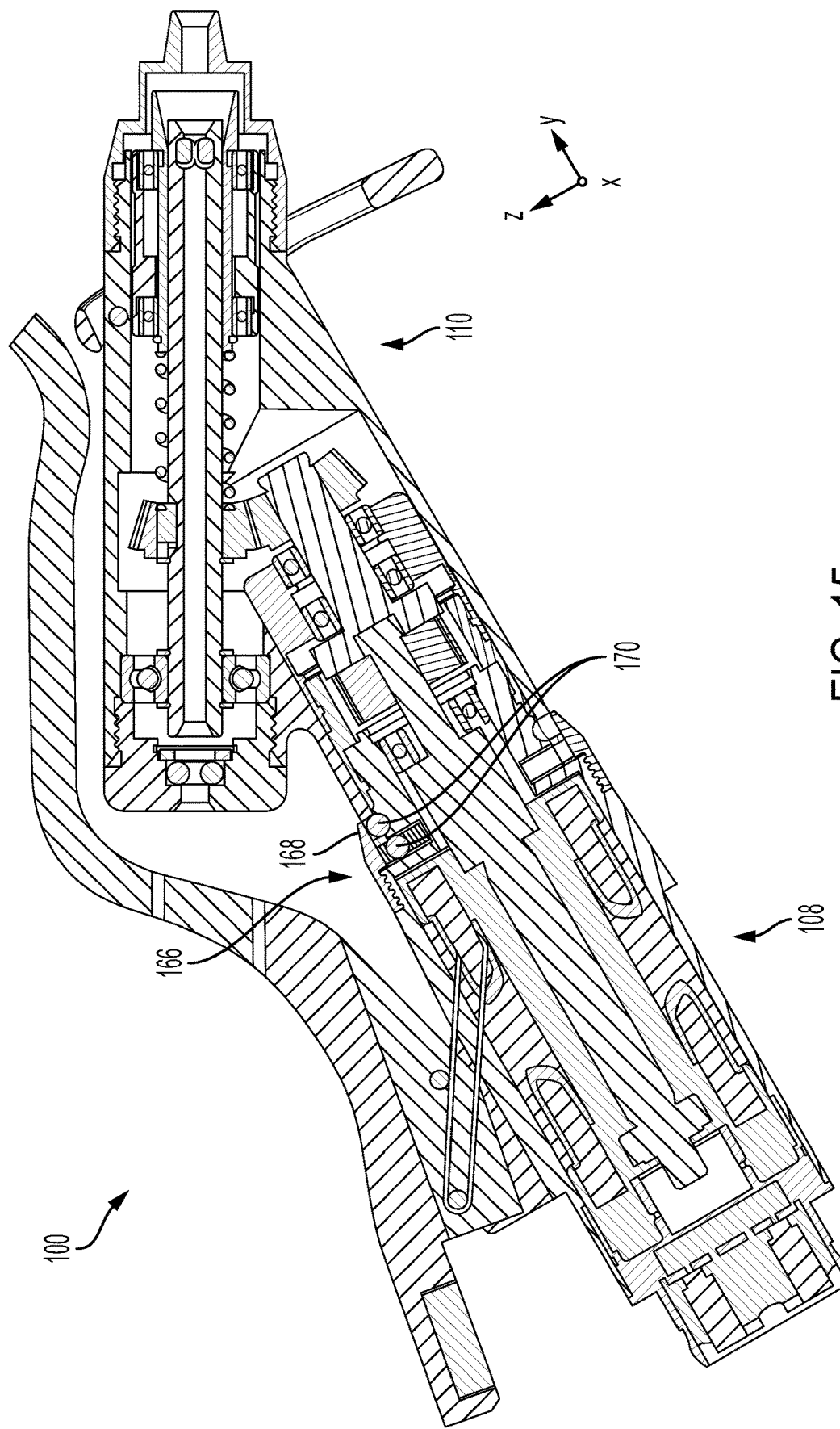
FIG. 15 is a cross-sectional side view schematic representation of the wire driver of FIG. 8.

An embodiment of the rotating (indexing) mechanism 166 is shown in FIG. 15. The gripping portion 110 rotates about the rotating (indexing) mechanism 166 relative to the handpiece 108. In FIG. 15, the rotating (indexing) mechanism 166 also maintains the connection between the gripping portion 110 and the handpiece 108 as the gripping portion 110 rotates. In the depicted embodiment, the rotating (indexing) mechanism 166 includes a ring 168 that extends around both the gripping portion 110 and the handpiece 108, holding them together. The rotating (indexing) mechanism 166 also includes one or more balls (or spheres) 170 between the ring 168 and both the gripping portion 110 and handpiece 108. The balls 170 rotate as the gripping portion 110 rotates around the handpiece 108. Thus, the balls 170 provide allow for movement of the gripping portion 110 about the handpiece 108, but the ring 168 limits the movement such that the gripping portion 110 does not become disconnected from the handpiece 108.

Figure 9:
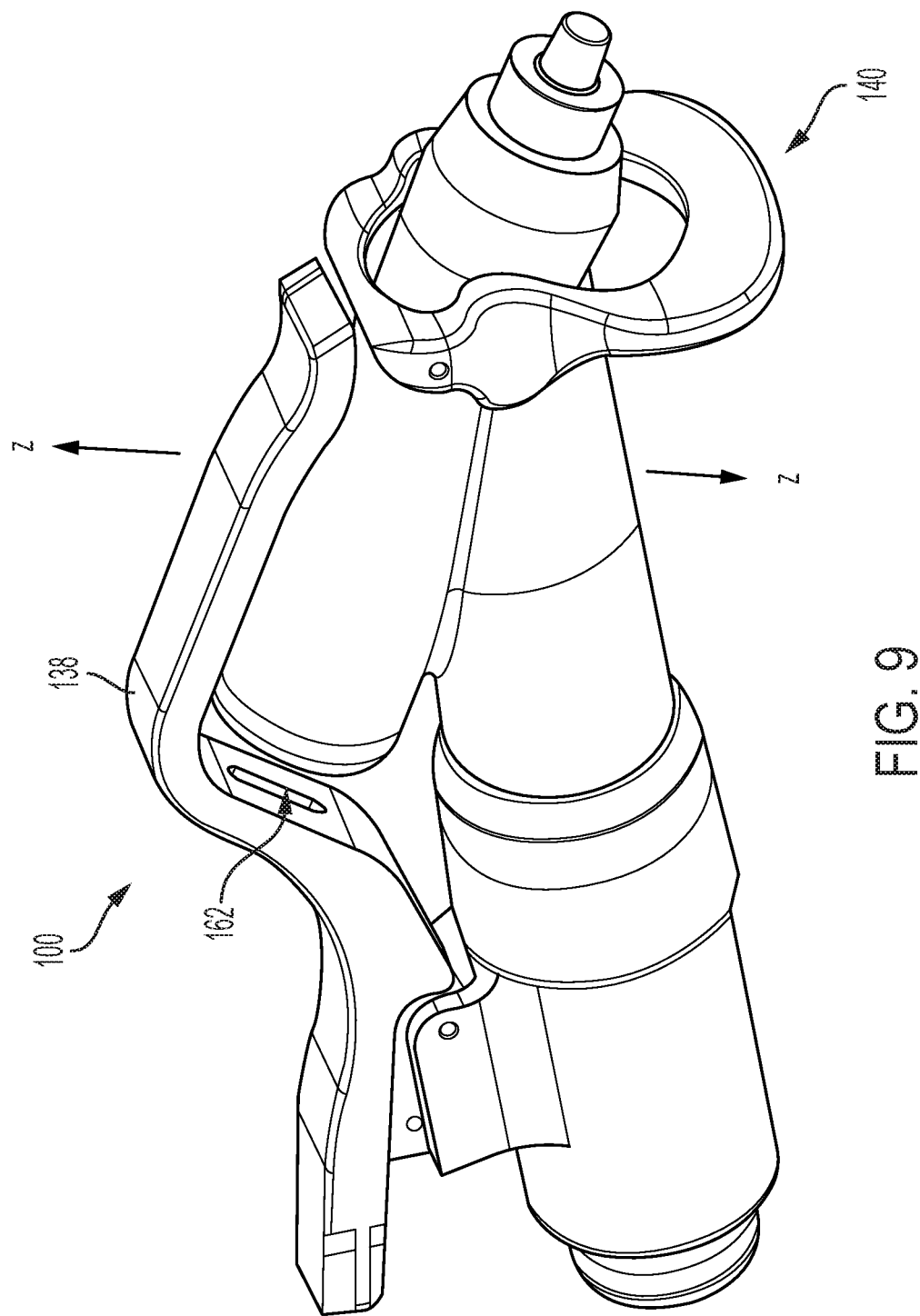
FIG. 9 is a perspective view schematic representation of the wire driver of FIG. 8.
Figure 10:
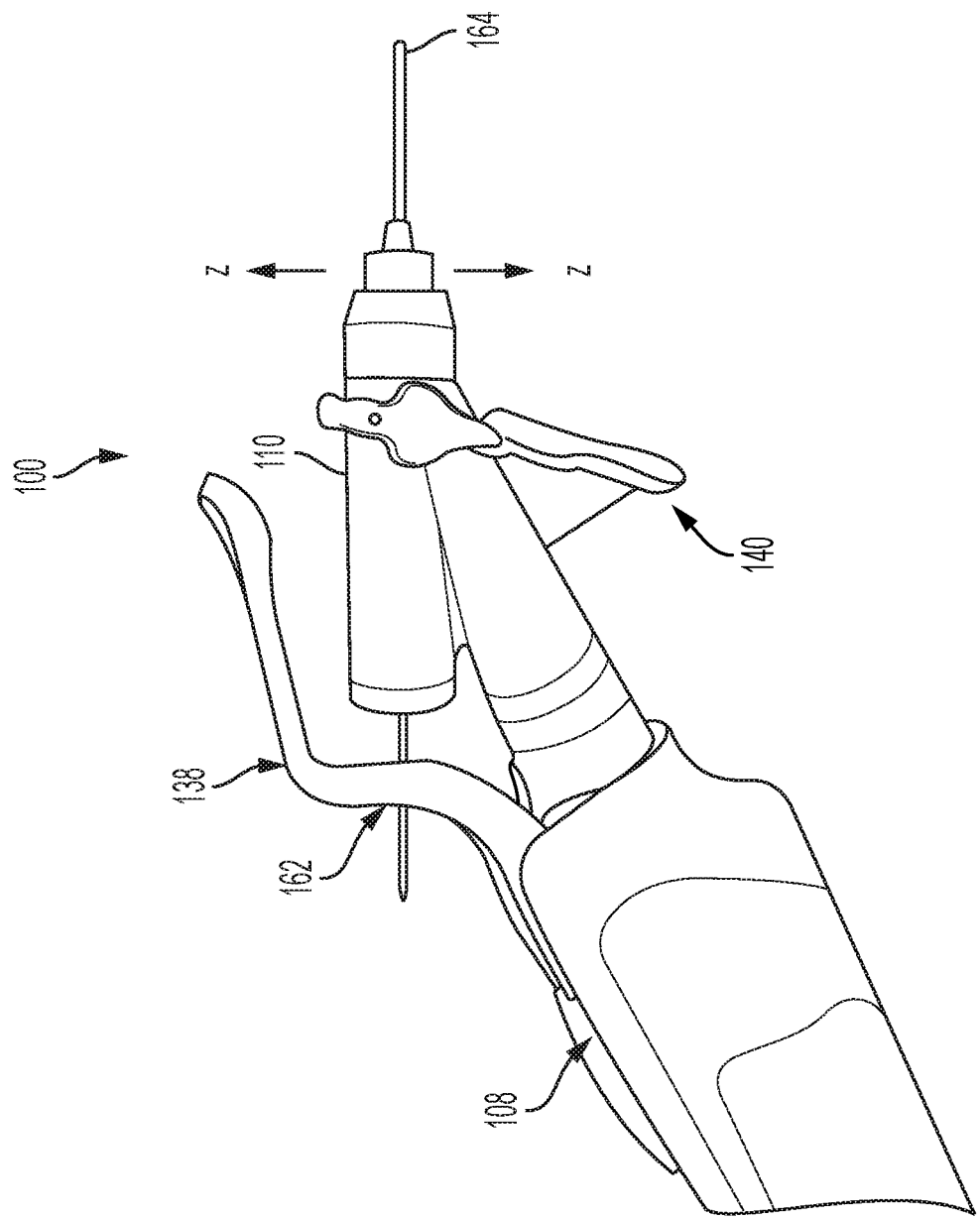
FIG. 10 is a side view schematic representation of the wire driver of FIG. 8 in a first configuration with a wire extending therethrough.
Figure 11:
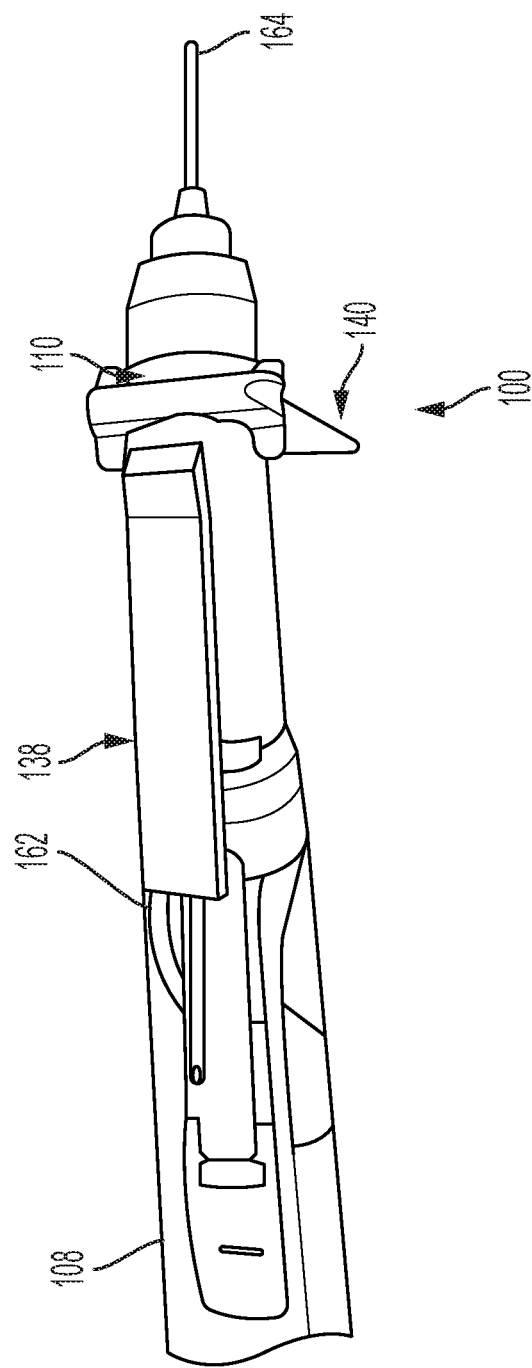
FIG. 11 is a top view schematic representation of the wire driver of FIG. 10.

FIG. 9 shows a perspective view schematic representation of the wire driver 100. As shown, the driving actuator 138 comprises an opening 162 such that the wire (not shown) may extend therethrough. In use, the wire 164 extends through the opening 162 in the driving actuator 138 and through the gripping portion 110, as shown in FIG. 10. In the first configuration, as shown in FIGS. 9 and 11, the opening 162 in the driving actuator 138 is aligned with the gripping portion 110 such that the wire 164 may extend through both the opening 162 and the gripping portion 110. Moreover, in the first configuration, the driving actuator 138 is in the same plane (along plane z-z) as the handpiece 108 and the gripping portion 110.

Figure 12:
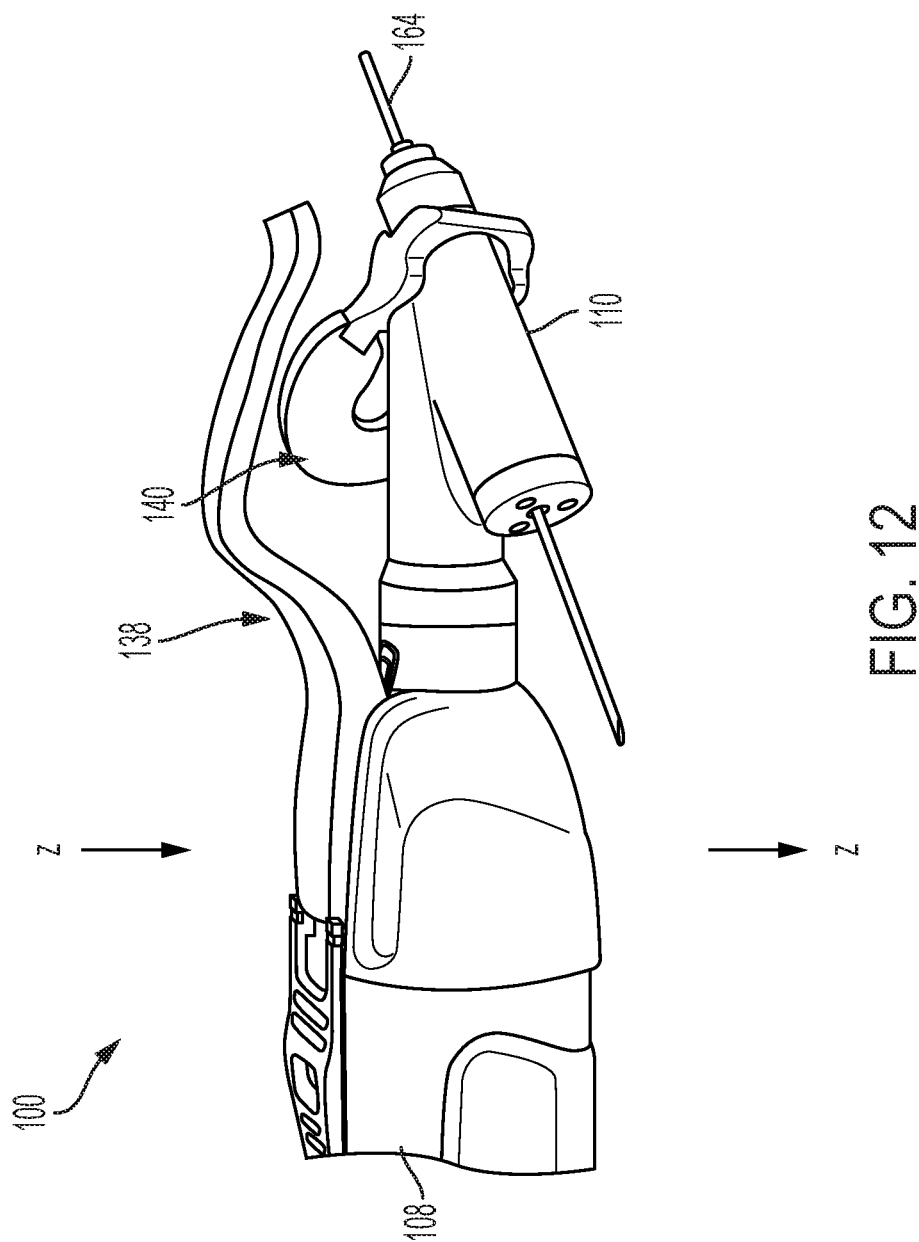
FIG. 12 is a side view schematic representation of the wire driver of FIG. 8 in a second configuration with a wire extending therethrough.
Figure 13:
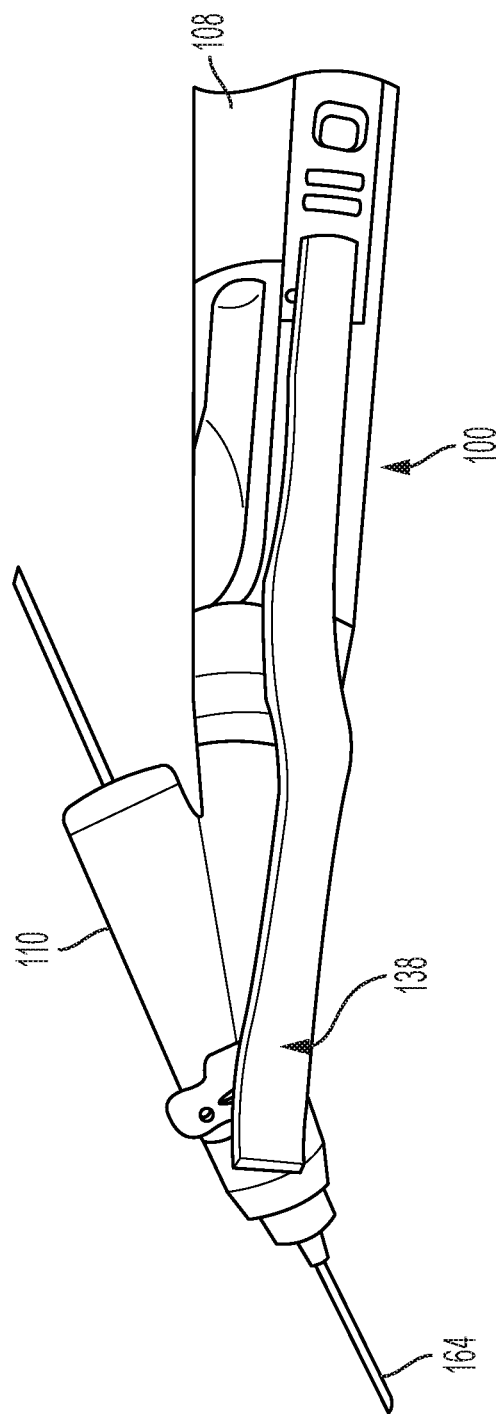
FIG. 13 is a top view schematic representation of the wire driver of FIG. 11.
Figure 14:
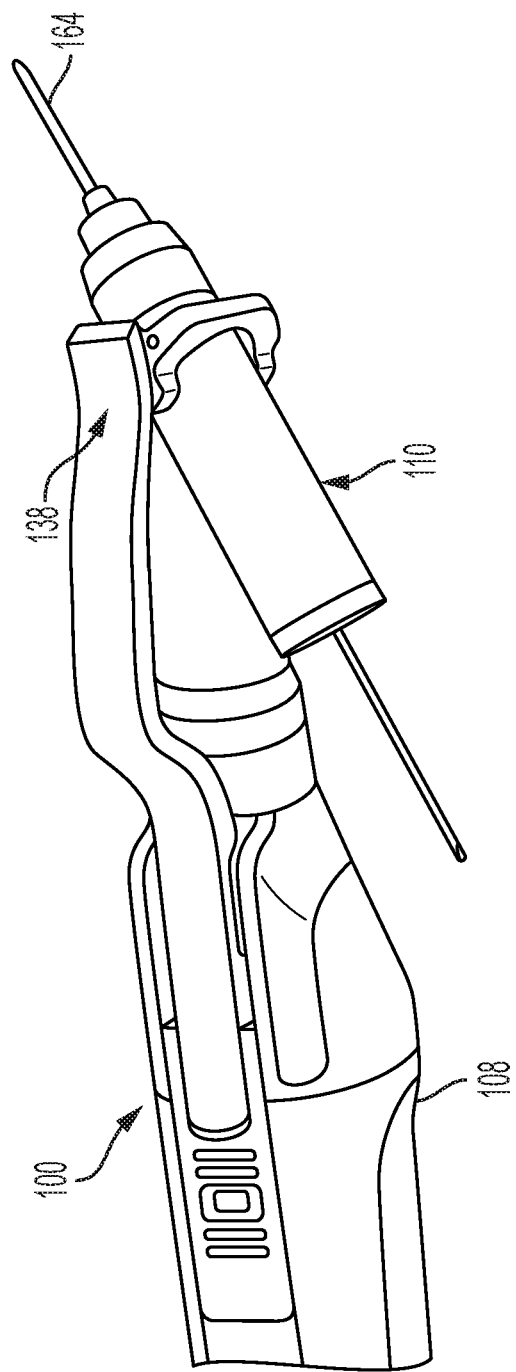
FIG. 14 is another top view schematic representation of the wire driver of FIG. 11.

FIGS. 12-14 show various views schematic representations of the wire driver 100 in a second configuration. In the second configuration, the gripping portion 110 is rotated about the rotating mechanism (not shown) out of plane z-z. In the depicted embodiment, the gripping portion 110 has been rotated 90° relative to plane z-z. However, the gripping portion 110 may be rotatable to any angle relative to the plane z-z. The rotating mechanism (not shown) allows the flexibility of the user (e.g., surgeon) to grip the handpiece 108 according to his or her personal preference and for greater comfort. Further, if the user selects an overhand grip to hold the wire driver 100, as shown in FIGS. 10 and 11, the wire 164 can be hazardous because it is directly in line with the palm of the user's hand. As surgical wires 164 typically have pointed tips at both ends, the proximal tip can puncture the surgeon's glove and/or cause injury. Thus, the rotating mechanism (not shown) also serves as a safety feature of the wire driver 100 in FIGS. 8-14.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A wire driver, comprising:
    a housing having a proximal end and a distal end, the housing comprising a handpiece extending from the proximal end to a gripping portion, wherein the gripping portion extends to the distal end;
    a channel extending through the gripping portion;
    a gripping mechanism connected to the channel;
    a first actuator connected to the distal end of the housing and the gripping mechanism;
    wherein the first actuator is movable between a relaxed position and a compressed position; and
    a spring assembly within the gripping portion, the spring assembly connected to the gripping mechanism, wherein when the first actuator is in the compressed position, the spring assembly is compressed and the gripping mechanism is in an open position.

2. The wire driver of claim 1, wherein in the relaxed position, the gripping mechanism is closed.

3. The wire driver of claim 1, further comprising a drive mechanism positioned within the handpiece and connected to the channel, wherein the drive mechanism is configured to rotate the channel when actuated by a second actuator connected to the handpiece.

4. The wire driver of claim 3, wherein the second actuator extends along the handpiece and at least a portion of the gripping portion.

5. The wire driver of claim 1, wherein the gripping portion extends along a first central longitudinal axis.

6. The wire driver of claim 5, wherein the handpiece is connected to the gripping portion at an angle relative to the first central longitudinal axis.

7. The wire driver of claim 5, wherein the handpiece extends along a second central longitudinal axis, which is parallel to the first central longitudinal axis.

8. The wire driver of claim 1, further comprising a spring assembly within the gripping portion, the spring assembly connected to the gripping mechanism.

9. The wire driver of claim 1, further comprising a rotating mechanism within the housing, wherein the gripping portion is rotatable about the rotating mechanism relative to the handpiece.

10. A powered surgical tool, comprising:
    a housing having a proximal end and a distal end, the housing comprising a handpiece extending from the proximal end to a gripping portion, wherein the gripping portion extends to the distal end;
    wherein the gripping portion extends along a central longitudinal axis and the handpiece is connected to the gripping portion at an angle relative to the central longitudinal axis;
    a spring assembly within the gripping portion, the spring assembly connected to the gripping mechanism, wherein when the first actuator is in the compressed position, the spring assembly is compressed and the gripping mechanism is in an open position; and
    a rotating mechanism positioned within the housing, wherein the gripping portion is rotatable about the rotating mechanism relative to the handpiece.

11. The surgical tool of claim 10, further comprising a channel extending through the gripping portion and a gripping mechanism connected to the channel.

12. The surgical tool of claim 11, further comprising a first actuator connected to the gripping portion and to the gripping mechanism, wherein the first actuator is movable between a relaxed position and a compressed position and in the relaxed position, the gripping mechanism is closed.

13. The surgical tool of claim 11, further comprising a drive mechanism positioned within the handpiece and connected to the channel, wherein the drive mechanism is configured to rotate the channel when actuated by a second actuator connected to the handpiece.

14. The surgical tool of claim 13, wherein the second actuator extends along the handpiece and at least a portion of the gripping portion.

15. The surgical tool of claim 13, wherein the second actuator comprises an opening extending therethrough.

16. The surgical tool of claim 15, wherein the gripping portion is rotatable between a first position and a second position.

17. The surgical tool of claim 16, wherein in the first position, the opening in the second actuator is aligned with the channel in the gripping portion.

18. The surgical tool of claim 17, wherein in the second position, the opening in the second actuator is not aligned with the channel in the gripping portion.

19. The surgical tool of claim 16, wherein in the first position, the gripping portion and the handpiece extend in the same plane.

* * * * *